United States Patent [19]

Battersby et al.

[11] Patent Number: 5,130,255
[45] Date of Patent: Jul. 14, 1992

[54] PROCESS FOR PREPARING STORAGE STABLE PHARMACEUTICALS

[75] Inventors: John E. Battersby; William S. Hancock, both of Hillsborough; Virgil B. Lawlis, Jr., San Mateo, all of Calif.

[73] Assignee: Genentech, Inc., South San Francisco, Calif.

[21] Appl. No.: 627,287

[22] Filed: Dec. 13, 1990

[51] Int. Cl.$^5$ .............................................. G01N 33/68
[52] U.S. Cl. ........................................ 436/55; 424/2; 436/86; 436/128; 436/183
[58] Field of Search ................... 436/55, 86, 128, 130, 436/161, 183; 424/2

[56] References Cited

U.S. PATENT DOCUMENTS

| | | |
|---|---|---|
| 2,649,090 | 8/1953 | Parsons et al. . |
| 2,652,182 | 9/1953 | Umbdenstock . |
| 2,698,272 | 12/1954 | Clapp et al. . |
| 3,198,368 | 8/1965 | Kirkland et al. . |
| 3,313,439 | 4/1967 | Robinson . |
| 3,424,329 | 1/1969 | Hershberg et al. . |
| 3,552,591 | 1/1971 | Wimmer . |
| 4,105,701 | 8/1978 | Larkin ............................. 560/248 X |
| 4,397,903 | 8/1983 | Allen et al. . |
| 4,413,070 | 11/1983 | Rembaum ....................... 435/180 X |
| 4,414,309 | 11/1983 | Langen et al. . |
| 4,691,034 | 9/1987 | Sanderson et al. . |
| 4,713,346 | 12/1987 | Gallop et al. ................... 436/128 X |

FOREIGN PATENT DOCUMENTS 8809323 12/1988 World Int. Prop. O. .

*Primary Examiner*—Robert J. Hill, Jr.
*Attorney, Agent, or Firm*—Max D. Hensley; Nancy A. Oleski

[57] ABSTRACT

Container systems for stable storage of pharmaceutical compounds are disclosed. The container systems prevent the formation of adducts between pharmaceutical compounds and aldehydes during storage of these compounds in containers sealed with elastomeric stoppers that leach aldehydes. Methods for determining the presence of these adducts are also disclosed.

18 Claims, 3 Drawing Sheets

PROCESS FOR PREPARING STORAGE STABLE PHARMACEUTICALS

BACKGROUND OF THE INVENTION

I. Field of the Invention

This invention relates to systems for storing pharmaceutical compounds. Specifically, the invention relates to combinations and methods for preventing the formation of aldehyde adducts of pharmaceutical compounds.

II. Description of Background and Related Art

It is conventional to store pharmaceuticals in glass vials stoppered with an elastomeric plug. The plug seals the vial while providing access for hypodermic needles. Considerable effort has been expended in the past in modifying such elastomeric stoppers.

U.S. Pat. No. 2,652,182 discloses coating rubber stoppers with silicone oil, vegetable oil, or certain esters to prevent the stoppers from adhering to each other when used in machines for automatically and mechanically stoppering vials.

U.S. Pat. No. 2,649,090 discloses a rubber stopper coated with a moisture-resistant, oily silicone lubricant to prevent the stopper form absorbing moisture by rendering it moisture-resistant.

U.S. Pat. No. 2,698,272 discloses coating an elastomeric stopper with a film of nylon or other thermoplastic synthetic resin to provide a method of forming a needle-penetrable sealing cap or stopper for a bottle.

U.S. Pat. No. 3,198,368 discloses a means for sealing a container comprising an inner layer of a tetrafluoroethylene polymer, and an outer layer of natural rubber superimposed over the inner layer. This combination of inner and outer layers permits the stopper to be punctured several times while maintaining sterile conditions inside the container.

U.S. Pat. No. 3,313,439 discloses a protective cap fitted on the internal surface of a rubber stopper to prevent the stopper from coming into contact with the contents of the container, thus serving to maintain the sterility of the solution inside the container. The cap is made of a thermoplastic material such as polypropylene or polyethylene.

U.S. Pat. No. 3,552,591 discloses a Teflon layer on the inner face of a rubber stopper. The Teflon layer is said to be less expensive than other materials, and permits a needle to be stuck through the entire stopper to withdraw the contents of the container.

U.S. Pat. No. 3,424,329 discloses a disc made of a fluorcarbon plastic that is placed on the inner face of an elastomeric stopper to reduce the potential for the contamination of the container contents.

U.S. Pat. No. 4,397,903 disclose a Teflon lining for the inner surface of an elastomeric stopper. This lining serves to aid in keeping the solution within the container sterile.

None of these improvements have been concerned with the leaching of gases from the elastomer, nor have others in the art known to the inventors identified any problem attendant the leaching of gases from elastomeric stoppers in the field of pharmaceutical containers.

SUMMARY OF THE INVENTION

This invention is based on the inventors discovery that certain pharmaceutical compounds stored in containers that are sealed with conventional elastomeric stoppers react with aldehydes leached from the stopper to form covalent adducts during storage. Under conventional storage conditions, the aldehyde reacts with primary and/or secondary amine groups and perhaps other functional groups on the pharmaceutical compound to form aldehyde adducts. The aldehyde adducts are undesirable in that they may exhibit chemical and physical properties that are different from the unmodified pharmaceutical compound. Thus, spontaneous formation of the aldehyde adduct during the storage of pharmaceuticals is especially problematic. The purity and uniformity of the pharmaceutical compound is particularly important when the compound is to be administered to animals and/or humans, as derivatized forms of the compound may alter its efficacy. These and other potential problems resulting from the presence of pharmaceutical compound aldehyde adducts are overcome in practicing this invention.

In accordance with this invention, methods are provided comprising determining whether the pharmaceutical compound is susceptible to aldehyde adduct formation, and, if so, disposing and storing the pharmaceutical compound in a container under conditions such that it does not react with aldehydes that are spontaneously released by the elastomeric stopper used to seal the container. Several general approaches are available to prevent adduct formation.

In one preferred embodiment, a barrier is interposed between the elastomeric stopper and the pharmaceutical compound, and the barrier is impermeable to aldehyde gases. In this respect this embodiment is essentially a mechanical barrier. One skilled in the art can readily identify suitable materials that are impermeable to aldehyde gases.

In another preferred embodiment, an aldehyde scavenger is applied to the surface of the elastomeric stopper or combined with the pharmaceutical compound. It is believed that the scavenger functions by reacting with aldehydes and renders them inert such that the aldehydes cannot form adducts with the pharmaceutical compound.

In another preferred embodiment, once the susceptibility of the pharmaceutical compound to adduct formation has been determined, one can simply select an elastomeric stopper that does not emit aldehydes, or that emits insufficient amounts of aldehydes to form adducts.

In one other preferred embodiment, the amine groups are protonated to render them unsusceptible to adduct formation.

DETAILED DESCRIPTION OF THE INVENTION

I. Definitions

Figure 1:
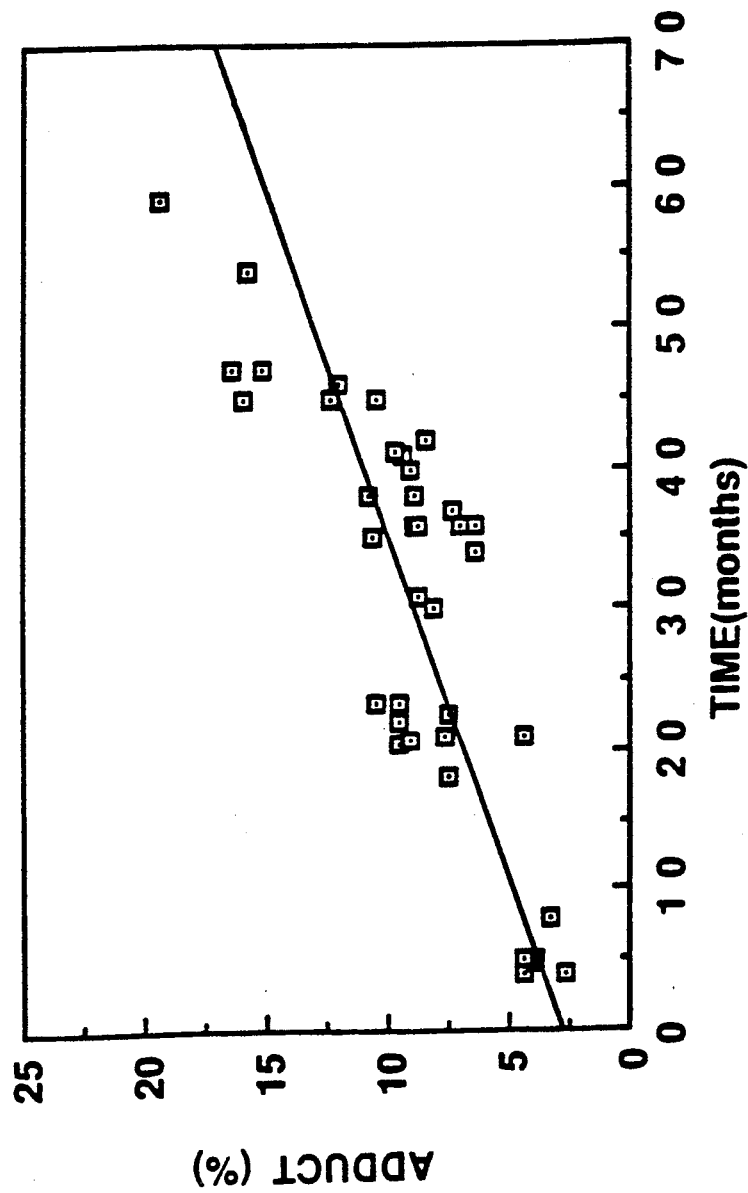
FIG. 1 depicts the amount of adduct formed over time between recombinant human growth hormone (hGH) and acetaldehyde when the hGH is stored in the lyophilized form in a container sealed with an otherwise conventional elastomeric stopper that has been found to emit acetaldehyde.

The term "aldehyde adduct" refers to a chemical addition reaction between an aldehyde and a pharmaceutical compound. The aldehyde may be any aldehyde, although typically it is formaldehyde, acetaldehyde, propionaldehyde, butyraldehyde, or benzaldehyde. The aldehyde normally adds to primary and/or secondary amine functional groups present on the pharmaceutical compound to form the adduct. Pharmaceutical compounds that are proteins usually have a primary amine group present at the amino terminus of the protein and also on the side chain of lysine. Non-proteinaceous pharmaceuticals may have reactive primary and/or secondary amine groups variously located on the molecule. The aldehyde is believed to bind to the primary amine group via an aldimine (Schiff base) linkage. Aldehydes may also form adducts with pharmaceutical compounds containing alcohol functional groups. The aldehyde bonds to the alcohol functional group through a hemiacetal linkage. For protein pharmaceuticals, the side chains of the amino acids serine, threonine, and tyrosine possess alcohol functional groups and are thus subject to adduct formation via the hemiacetal linkage. The thiol functional groups of pharmaceutical compounds are also subject to aldehyde adduct formation through a thio-hemiacetal linkage. Protein pharmaceuticals that possess amino acids with side chains containing thiols (such as cysteine) may form thio-hemiacetal adducts.

The aldehyde adducts will typically form between lyophilized or powdered pharmaceuticals and aldehydes in the gaseous state. However, the adducts may also form when either the aldehyde is a liquid and the pharmaceutical is a solid, or when the aldehyde is gaseous and the pharmaceutical is a liquid, or when both components are dissolved in solvents or are liquids, as the case may be where a liquid formulation leaches aldehyde from the stopper. Formation of the adduct will depend in part on the concentration of the pharmaceutical relative to the concentration of the aldehyde. A large excess of aldehyde can drive the formation of the adduct, while a large excess of the pharmaceutical can result in less adduct being formed.

The aldehyde adducts described herein may be represented by either formula I or formula II below:

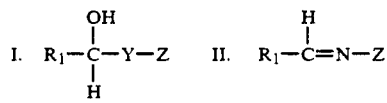

In formula I, R1 may be H, a lower alkyl, or a $C_6$–$C_{10}$ aryl; Y is O or S; and Z is a pharmaceutical compound.

In formula II, R1 may be H, a lower alkyl, or $C_6$–$C_{10}$ aryl; and Z is a pharmaceutical compound.

These adducts are only examples. Other reaction products may be identified in the future and these are included within the group of undesirable products that it is the object herein to prevent.

The term "elastomeric stopper" refers to an article that is used to seal vials or containers ordinarily employed for sterile pharmaceutical products, and is made of natural or synthetic rubber, or a natural or synthetic rubber blend.

The term "lyophilized" refers to the physical state of a chemical compound. A lyophilized compound is produced by drying the compound (normally frozen) under vacuum to remove a substantial portion of the moisture, and the resulting compound is in a low moisture solid state. A lyophilized compound will ordinarily be less than ten percent moisture by weight.

The term "recombinant protein" refers to a protein that is produced using recombinant DNA technology. The DNA (usually cDNA) encoding the protein of interest is transformed into a suitable host cell, and the host cell synthesizes the protein. The protein is then isolated using appropriate methodology, and is tested for biological activity.

II. Formation of the Pharmaceutical-Aldehyde Adduct

The pharmaceutical compounds included within the scope of this invention are those that have one or more functional groups as described above that render them susceptible to aldehyde adduct formation. Particularly preferred pharmaceuticals are those that are stored in the powdered or lyophilized form in containers that are sealed with elastomeric stoppers. More preferred are those pharmaceuticals that have primary or secondary amine functional groups, including proteins and some non-proteinaceous compounds such as certain antibiotics, steroids, antihistamines, vasodilators, vasoconstricters, smooth muscle relaxants, diuretics, sedatives, hormones, and antihypertensives. The most preferred non-proteinaceous compounds are penicillamine, penicillin, gentamycin, theophylline, epinephrine, thyroxine, dopamine, sphingosine, gamma-amino butyric acid, and taurine.

The preferred protein pharmaceuticals of this invention are those that are produced by recombinant DNA methodology, have at least a primary and/or secondary amine group at the amino terminus and/or one or more amino acids along the polypeptide chain with a functional primary amine group, a functional alcohol group, and/or a functional thiol group. More preferred are those proteins that are used as pharmaceuticals and are packaged and stored in the lyophilized form. Yet more preferred are those proteins with methionine as the amino terminal amino acid. The most preferred proteins of this invention are recombinant human growth hormone and recombinant gamma-interferon. The protein can be sterile and the pharmaceutical preparation can be more than 99 percent pure by weight of protein.

In general, we have found that elastomeric stoppers can emit from 0 to 0.50 parts per million (ppm) acetaldehyde, depending in part on the chemical composition of the stopper. The rate of emission of acetaldehyde from the stopper may be constant over time or it may vary as a function of the exact composition of the stopper and the temperature at which the stopper is kept. Although the precise mechanism by which acetaldehyde is emitted is unclear, it is anticipated that the amount of acetaldehyde emitted by the stopper would be increased at higher temperatures. The stability of the aldehyde-pharmaceutical adduct over time is expected to vary with the storage temperature. Lyophilized recombinant human growth hormone disposed in a container and sealed with a stopper that emits acetaldehyde will form levels of adduct after one month of storage at 2°–8° C. which are detectable by ion exchange chromatography.

Formation of the aldehyde adduct is affected by pH. At acidic pH values, some or all of the primary amine group(s) can become protonated (depending on the pKa of the amine group and the pH of the solution) such that they have a net positive charge. These positively charged primary amine groups are generally not subject to addition reactions with aldehydes.

Methods for determining the presence of the pharmaceutical-aldehyde adduct are known in the art. These methods include, but are not limited to, ion exchange chromatography, size exclusion chromatography, and liquid chromatography, including reverse phase liquid chromatography. Each of these methods may be performed using conventional chromatographic means or using high performance chromatographic methodology. In addition, the presence of the adduct may be determined by colorometric analysis using, for example, dinitrophenylhydrazine. Another useful method for determining the presence of the adduct involves dissolving the adduct in solution to dissociate the aldehyde from the pharmaceutical, and analyzing the solution for the presence of adduct-free pharmaceutical and free aldehyde. One other useful method for analysis is mass spectrometry.

The preferred methods for determining the presence of the adduct include ion exchange chromatography, including high performance ion exchange chromatography, and reverse phase high performance liquid chromatography.

Ion exchange chromatography, including high performance ion exchange chromatography, is well known in the art (see Hancock, ed. *CRC Handbook of HPLC for the Separation of Amino Acids, Peptides, and Proteins*, CRC Press, Boca Raton, Fla. [1984]) for a general description of this method). For analysis of pharmaceutical-aldehyde adducts, a suitable resin is selected primarily based on the net charge of the pharmaceutical, however, size, hydrophobicity and other characteristics of the pharmaceutical are also typically considered. A solvent system for binding the pharmaceutical of interest to the resin is then selected based on the characteristics of the pharmaceutical and the resin. This selection can readily be accomplished without undue experimentation. A suitable solvent system is, for example, a phosphate buffer (or other appropriate organic or inorganic salt buffer) at a concentration of at least 40 mM, in combination with an organic solvent (such as, for example, acetonitrile, methanol, or propanol) at a pH that is slightly acidic (i.e., a pH of less than about 6.5). An elution buffer is also selected based on the characteristics of the pharmaceutical including its net charge and hydrophobicity. A typical elution buffer is similar in composition to the binding buffer, but may have a different pH and/or ionic strength, or may otherwise be modified. Suitable elution rates for the sharpest resolution between the pharmaceutical and the pharmaceutical-aldehyde adduct can easily be determined without undue experimentation. The elution profile may be monitored by any suitable means, including, for example, absorbance of amide bonds at 214 nm for protein pharmaceuticals, or monitoring aromatic rings in the pharmaceutical that absorb at 280 nm.

High performance liquid chromatography and reverse phase high performance liquid chromatography in general are described in *HPLC Analysis of Biological Compounds* (Hancock and Sparrow, eds., Marcel Dekker, Inc., New York [1984]). Typically, a column is selected based on the size, hydrophobicity, and other characteristics of the pharmaceutical. Similarly, the solvent systems used will be selected based on the characteristics of the pharmaceutical. In general, the solvent systems used are a combination of a solvent modifier (such as trifluoroacetic acid or acetic acid) and an organic modifier (such as acetonitrile, methanol and propanol). The elution profile can be monitored by any appropriate method as previously described.

III. Preventing Formation of the Adduct

A. Barriers to Aldehyde Diffusion

In a first embodiment, mechanical barriers are situated between the elastomeric stopper and the pharmaceutical to prevent aldehydes from contacting the pharmaceutical. In one instance, the barrier comprises a coating on the stopper that is impermeable to aldehydes. The stopper may be completely coated, or the coating may be confined to the area of the stopper that faces the interior of the container. The coating may be any substance, preferably in the liquid form (for ease of coating) that, when applied to the stopper, forms an impermeable barrier to aldehydes. The coating will be applied at a thickness that is sufficient to form a satisfactory barrier without affecting the tightness of the seal around the mouth of the container formed by the stopper. A suitable barrier will be a metal foil or a thixotropic mixture containing a scavenger as described infra (e.g. with polyvinyl alcohol or a sugar alcohol), or impregnated film (e.g. polyacrylamide).

The effectiveness of a substance used as a barrier to aldehydes can be determined as follows. The substance is first applied to the stopper. If the substance is in a liquid form when applied, it is allowed to dry. The stopper is then placed onto the container and left for a period of time. Over time (daily or weekly, for example), samples of gas are withdrawn from the container using a hypodermic needle attached to a syringe. The composition of the gas is then analyzed using an appropriate method such as gas chromatography. The presence of aldehydes in the sample is assessed by reference to the retention times of aldehyde standards.

An alternative method to evaluate the effectiveness of the selected substance to act as a barrier to aldehydes is to seal the pharmaceutical-containing container with the stopper, the stopper having been previously coated with the substance to be evaluated. After a suitable period of time, the pharmaceutical is tested for the presence of aldehyde adducts using, for example, high performance ion exchange chromatography. If no adduct is detected, the substance may be deemed suitable as an effective barrier to acetaldehyde, provided that the pharmaceutical has previously been shown to form the adduct.

B. Use of Scavengers

Another embodiment of the present invention is directed to the use of a scavenger to prevent the aldehydes released from the stopper from forming adducts with the pharmaceutical stored in a container that is sealed with the stopper. For purposes of this application, a scavenger is a chemical substance that acts to remove or make inert a second chemical substance that is deemed undesirable because of its potential to react with a desired pharmaceutical compound. The scavenger acts to modify the reactive functional group(s) of the undesirable compound to render them inert with respect to the pharmaceutical compound. Alternatively, the scavenger may act by shifting the reaction equilibrium away from formation of an adduct between the undesired compound and the pharmaceutical and toward formation of a complex between the scavenger and the undesired compound. Normally, a stable bond forms between the scavenger and the reactive group of the undesired compound so that it is no longer reactive with the pharmaceutical. The scavenger contains reactive primary and/or secondary amine, sulfhydryl, hydroxyl and/or other functional groups found on pharmaceutical compounds that ordinarily react with aldehydes. By way of illustration, a scavenger for aldehydes normally will contain primary amine groups that react with aldehyde functional group(s) comprising the undesired compound so that the aldehyde is rendered inert with respect to the pharmaceutical.

The scavenger may be any substance (in a solid, liquid, or agseous state) that is reactive with aldehydes but that is not reactive with the pharmaceutical stored in the container, does not affect the activity of the pharmaceutical, and is pharmaceutically acceptable. Reactive is defined as capable of forming a complex with an aldehyde. The complex may be linked through covalent, hydrogen, dipole-dipole, ionic, ion-dipole, and/or van der Waals interactions. The reactivity of the scavenger towards aldehydes will be dependent in part on the structure of the scavenger. Smaller molecules that are primary amines are preferred as scavengers as they are less sterically hindered and can more readily react. Also preferred are scavengers that are primary amines and that display greater basicity (surrounded by one or more electron donating groups such as alkyl groups) as such molecules are more reactive towards aldehydes. Most preferred as a scavenger is methioninamide although it will be understood that functionally equivalent compounds can be employed.

Scavengers of aldehydes are known in the art. U.S. Pat. No. 4,691,034 discloses the use of bisulphite salts as acetaldehyde scavengers. The use of water-soluble active methylene compounds as scavengers of formaldehyde is disclosed in WO 809323 (published Dec. 1, 1988).

In one embodiment, the scavenger is in the form of a solid compound, and is admixed directly with the lyophilized or powdered pharmaceutical. Since a desired scavenger has a lower molecular weight than the pharmaceutical, the scavenger is preferably added at a greater molar concentration than the pharmaceutical, generally at a molar ratio of at least about 10:1. Since more scavenger than pharmaceutical will be present on a molar basis, there is a greater probability that the aldehyde will form a complex with the scavenger as compared to the pharmaceutical. The optimal molar ratio may be experimentally determined without undue experimentation. A series of concentrations of scavenger can simply be admixed with the pharmaceutical, and the amount of pharmaceutical-aldehyde adduct can subsequently be determined using methods described above. The optimal concentration of scavenger will be that which best protects the pharmaceutical from adduct formation.

In another embodiment, the scavenger is applied directly to the stopper by coating the stopper with a suitable formulation that contains the scavenger. The coating thus provides a localized concentration of scavenger in the vicinity of the stopper aldehyde emissions. The scavenger is preferably in either a liquid or a solid form. Application of the scavenger to the stopper may be accomplished by first mixing the scavenger with a substance that adheres to the stopper, but that does not react with the scavenger. The mixture is then applied to the stopper and allowed to dry before the stopper is used to seal the container. This scavenger can form a complex with the aldehyde before the aldehyde comes into contact with the pharmaceutical. The effectiveness of the scavenger in preventing formation of the acetaldehyde adduct can be measured by analyzing a sample of the pharmaceutical for the adduct using ion exchange chromatography or HPLC as described above, or by other suitable methods.

C. Stoppers That Do Not Leach Aldehydes

A further embodiment of the present invention is directed to the use of elastomeric stoppers that do not leach aldehydes, or that do not leach sufficient amounts of aldehydes to form detectable levels of aldehyde adducts with pharmaceutical compounds disposed in containers that are sealed with the elastomeric stoppers. Stoppers that are suitable for this purpose may be tested as follows. The stopper is placed onto the container to form a tight seal. Over time, samples of gas are withdrawn from the interior of the container using a hypodermic syringe. The samples are then analyzed for the presence of aldehydes using gas chromatography or other suitable methods. If no aldehydes are detected, the stopper may be deemed suitable for practicing the invention. An alternative method for identifying suitable stoppers is to seal the container having the pharmaceutical disposed within it with the stopper. Over time, samples of the pharmaceutical are withdrawn and evaluated for the presence of adducts using methods described above. If no adduct is detected, the stopper is suitable for use.

D. Blocking Amine Functional Groups

One other embodiment of the present invention concerns blocking the amine groups that are susceptible to adduct formation. Any suitable blocking agent may be used for this purpose, however a preferred means of blocking susceptible primary and secondary amine groups is to protonate them. This protonation confers a net positive charge on the amine group. It is believed that the lone pair of electrons on the nitrogen atom of the amine, which are normally reactive towards carbonyl compounds, are rendered inactive towards electron acceptors upon protonation of the amine. Formation of the adduct is thus blocked by protonation.

Protonation of amine groups on the pharmaceutical compound may be accomplished by mixing the pharmaceutical with a buffer of a pH sufficient to protonate the labile amine groups. The mixture can be lyophilized without adversely affecting the protonation of the amine groups.

The following examples are intended as illustrative means of practicing the invention and should not be construed as limiting the invention.

EXAMPLES

I. Detection of the Adduct

Aliquots of 5 mg of lyophilized Protropin ® brand of human growth hormone (hGH) were disposed into glass vials and the vials were sealed with elastomeric stoppers ('890 Grey', obtained from The West Company, Phoenixville, PA). The vials were stored at 2°-8° C. for 5-60 months after which time the amount of hGH-acetaldehyde adduct formed was measured. Determination of the adduct was accomplished by high performance ion exchange chromatography (HPIEX) using a TSK-DEAE-3SW column (7.5mm by 75 mm, 10 micron particle size) and a Hewlett-Packard 1090 M HPLC system operating at a flow rate of 0.5 ml/min with detection set at 280 nm. Each aliquot of hGH was reconstituted with 5 ml of purified water to make a 1 mg/ml solution of hGH. A 50 μl sample was then injected onto the column. The column was pre-equilibrated with solvent A (66 mM potassium phosphate monobasic and 10% acetonitrile, pH 5.5). Elution of the protein-acetaldehyde adduct was accomplished with a linear gradient to 25% solvent B (66mM potassium phosphate monbasic, 10% acetonitrile, 0.2M ammonium acetate, pH 5.5) in a 20 minute period.

The results are shown in FIG. 1. It is apparent that the amount of acetaldehyde-protein adduct increases as a function of the amount of time the protein is stored in the container sealed with an elastomeric stopper that emits acetaldehyde. Scattering of data points around the line of best fit may be accounted for in part by the use of different production lots of the same stopper. Different lots have been shown to emit acetaldehyde at somewhat different rates.

II. Prevention of Formation of the Adduct

A. The Use of Methioninamide

To a 2 mg/ml solution of Protropin ® brand of hGH was added methioninamide to a final concentration of 100 mM. To minimize any possible ionic effects, the control solution received 100 mM NaCl instead of methioninamide. The pH of the mixture was adjusted to 7.4 using a 2M stock solution of TRIS buffer. A 5% solution of acetaldehyde was added to the hGH-methioninamide mixture to a final concentration of 0.05% (v/v) acetaldehyde. The solutions were kept at room temperature. Samples were withdrawn after 70 and 190 minutes and immediately desalted and buffer exchanged using PD-10 columns (Pharmacia) in a buffer containing 88 mM mannitol, 5 mM sodium phosphate, pH 7.8. The amount of adduct was then determined by using high performance ion exchange chromatography as described above.

Figure 2:
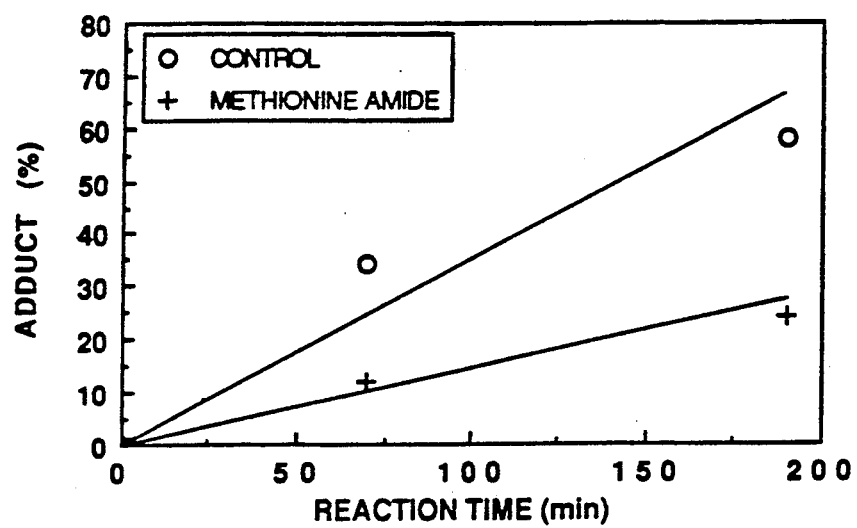
FIG. 2 depicts the effect of methioninamide, an acetaldehyde scavenger, on the formation of an adduct between human growth hormone and acetaldehyde.

The results are shown in FIG. 2. As can be seen, the samples that contained methioninamide had a lower rate of formation the of acetaldehyde adduct (expressed as percent of total protein that is in the acetaldehyde adduct form) as compared with the control samples.

B. Protonation of Amine Functional Groups

Figure 3:
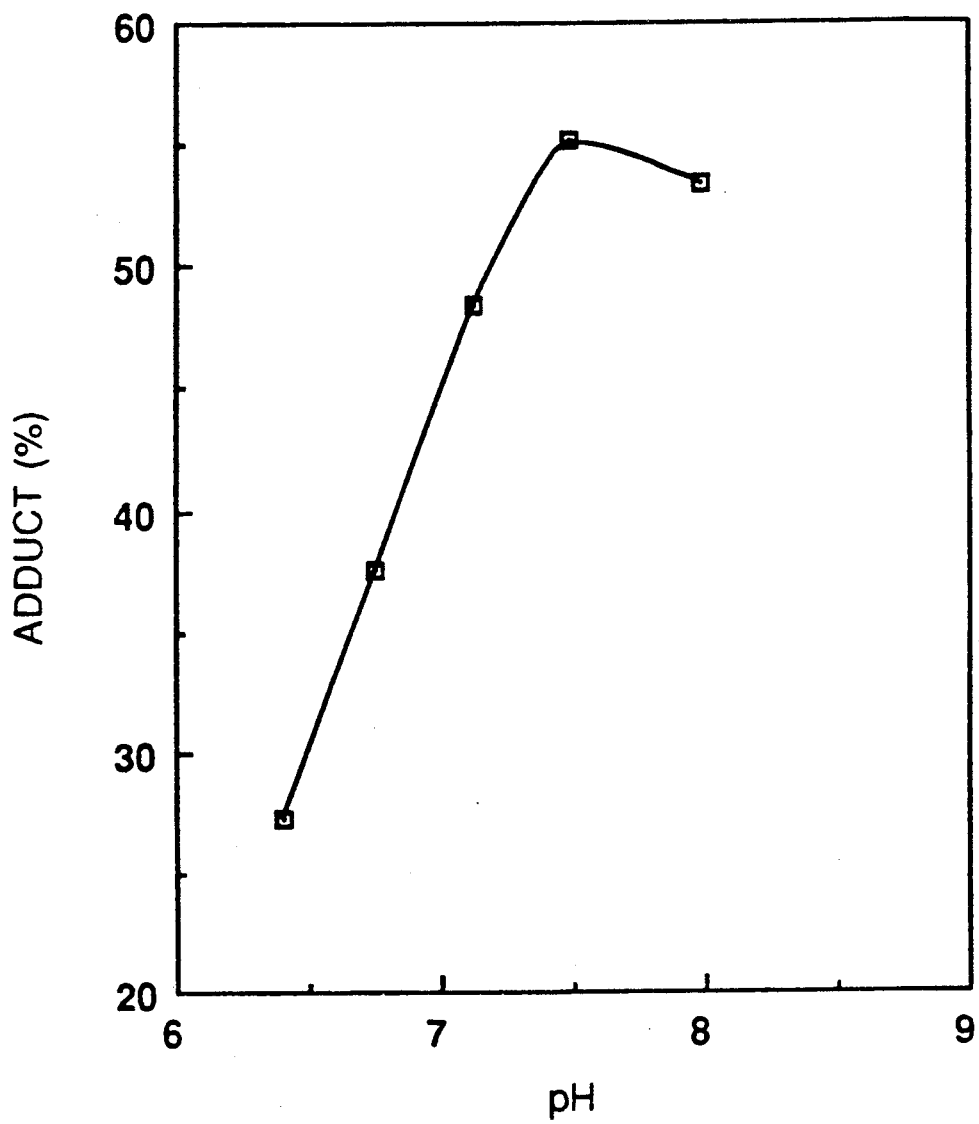
FIG. 3 depicts the effect of pH on the formation of the hGH-acetaldehyde adduct formation in solution.

To evaluate the effect of protonation of amine groups on acetaldehyde adduct formation, hGH was incubated in buffers at various pH values. For each sample, 10 ml of hGH in mannitol phosphate buffer was adjusted to the appropriate pH by the addition of either 0.1M Tris base or 0.1M phosphoric acid. A solution of 0.01% acetaldehyde (v/v) in water was then added. The samples were incubated at room temperature for 280 minutes. The reaction was terminated by freezing the samples in a dry ice/ethanol bath. Samples were stored at −70° C. prior to the analysis for the presence of hGH-acetaldehyde adduct formation. The analysis was conducted using the high performance ion exchange chromatography method as described above. The results are shown in FIG. 3. It is apparent that the amount of acetaldehyde-hGH adduct decreased as the pH of the solution dropped below 7.5.

We claim:

1. A method comprising:
  (a) contacting a protein with an aldehyde;
  (b) analyzing the protein for the presence of an aldehyde adduct; and
  (c) if an adduct is determined to be present in step (b), then disposing and storing a pharmaceutical preparation of said protein free of adduct in a container sealed with an elastomeric stopper under conditions such that the protein does not react with aldehyde emitted by the stopper.

2. The method of claim 1 wherein the protein is in a lyophilized state.

3. The method of claim 1 wherein the aldehyde is in the gaseous state.

4. The method of claim 1 wherein the protein is in a lyophilized state and the aldehyde is in a gaseous state.

5. The method of claim 1 wherein the aldehyde is acetaldehyde.

6. The method of claim 1 wherein the conditions include interposing a barrier for preventing the diffusion of gaseous aldehydes from the stopper to the protein.

7. The method of claim 1 wherein said conditions include combining the protein with an aldehyde scavenger.

8. The method of claim 7 wherein the aldehyde scavenger is methioninamide.

9. The method of claim 8 wherein the protein has an amino-terminal methionyl and is a product of recombinant cell culture.

10. The method of claim 9 wherein the protein is human growth hormone or gamma interferon.

11. The method of claim 1 wherein the conditions include employing a stopper that does not emit acetaldehyde.

12. The method of claim 1 wherein the pharmaceutical preparation is more than 99 percent pure by weight of protein.

13. The method of claim 12 wherein the protein is sterile.

14. The method of claim 1 wherein any aldehyde adduct of step (b) is analyzed by ion exchange chromatography.

15. The method of claim 1 wherein any aldehyde adduct of step (b) is analyzed by reverse high performance liquid chromatography.

16. A method comprising:
  (a) contacting a pharmaceutical with an aldehyde;
  (b) analyzing the pharmaceutical for the presence of an aldehyde adduct; and
  (c) if an adduct is determined to be present in step (b), then disposing and storing a preparation of said pharmaceutical free of adduct in a container sealed with an elastomeric stopper under conditions such that the pharmaceutical does not react with aldehyde emitted by the stopper.

17. The method of claim 16 wherein the pharmaceutical contains at least one amine group.

18. The method of claim 17 wherein the pharmaceutical is stored under conditions whereby the amine group is protonated.

* * * * *